United States Patent [19]

Waller

[11] Patent Number: 4,891,298

[45] Date of Patent: Jan. 2, 1990

[54] PHOTOGRAPHIC PRODUCTS AND PROCESSES

[75] Inventor: David P. Waller, Lexington, Mass.

[73] Assignee: Polaroid Corporation, Cambridge, Mass.

[21] Appl. No.: 252,663

[22] Filed: Oct. 3, 1988

[51] Int. Cl.$^4$ .................. G03C 5/54; G03C 5/26; C07D 311/78

[52] U.S. Cl. .................. 430/221; 430/236; 430/449; 430/486; 430/487; 549/281; 549/283; 549/290

[58] Field of Search ............... 430/221, 236, 449, 486, 430/487; 549/281, 283, 290

[56] References Cited

U.S. PATENT DOCUMENTS

| | | | |
|---|---|---|---|
| 3,415,644 | 12/1968 | Land | 430/220 |
| 3,415,645 | 12/1968 | Land | 430/220 |
| 3,415,646 | 12/1968 | Land | 430/220 |
| 3,647,437 | 3/1972 | Land | 430/221 |
| 3,702,244 | 11/1972 | Bloom et al. | 430/221 |
| 3,702,245 | 11/1972 | Simon et al. | 430/221 |
| 4,456,674 | 6/1984 | Cerankowski et al. | 430/221 |

*Primary Examiner*—Richard L. Schilling
*Attorney, Agent, or Firm*—Sybil A. Campbell

[57] ABSTRACT

This invention relates to diffusion transfer photographic processes adapted to be performed in the presence of ambient light and to diffusion transfer products useful in such processes wherein a substantial increase in opacification in the red and near infrared region of the visible spectrum and a substantial increase in opacification in the blue and green region is achieved by employing certain alkyl-substituted phenanthrol/carboxynaphthol phthaleins as the light-absorbing, pH-sensitive optical filter agent for the longer wavelength region of the visible spectrum.

30 Claims, 3 Drawing Sheets

PHOTOGRAPHIC PRODUCTS AND PROCESSES

BACKGROUND OF THE INVENTION

This invention relates to photography, and more particularly, it relates to photographic processes performed in ambient light and to photographic products useful in such processes.

A number of diffusion transfer processes for producing photographic images in both black-and-white and in color are now well known. Of particular interest are diffusion transfer processes wherein the image-receiving layer carrying the transfer image is not separated from the developed photosensitive layer(s) after processing but both components are retained together as a permanent laminate. Included as part of the laminate is a layer of a light-reflecting material, preferably titanium dioxide, positioned between the image-carrying layer and the developed photosensitive layer(s). The light-reflecting layer separating the image-carrying and photosensitive components provides a white background for the transfer image and masks the developed photosensitive layer(s). In addition to these layers, the laminate usually includes dimensionally stable outer layers or supports, at least one of which is transparent so that the resulting transfer image may be viewed by reflection against the background provided by the light-reflecting layer. Diffusion transfer processes for forming images viewable without separation of the photosensitive and image-receiving components and film units useful in such processes are described, for example, in U.S. Pat. Nos. 3,415,644, 3,415,645 and 3,415,656 issued Dec. 10, 1968 to Edwin H. Land.

U.S. Pat. No. 3,647,437 issued Mar. 7, 1972 to Edwin H. Land also is concerned with diffusion transfer processes wherein the resulting photograph comprises the developed photosensitive layer(s) retained with the image-receiving layer as part of a permanent laminate. In the processes disclosed in this patent, a photographic film unit comprising a photosensitive element is developed in ambient light but further undesired exposure during processing is prevented by a light-absorbing material or optical filter agent which is retained in the processed film unit. In a preferred embodiment, the optical filter agent is a pH-sensitive dye, i.e., a dye possessing spectral absorption characteristics that are reversibly alterable in response to changes in environmental pH and particularly, a pH-sensitive dye having a colored or light-absorbing form above a given alkaline pH and a colorless or non-light-absorbing form below said pH. In a particularly preferred embodiment, the film unit is of the type described in aforementioned U.S. Pat. No. 3,415,644 and comprises a first sheet-like component comprising an opaque support carrying a silver halide emulsion layer(s) and a second sheet-like component comprising a transparent support carrying an image-receiving layer which are in fixed relationship prior to exposure, which relationship is maintained after processing. After photoexposure through said transparent support, an aqueous alkaline processing composition is distributed in a thin layer between said components. The processing composition contains a light-reflecting pigment and at least one pH-sensitive dye which is in its colored form at the initial pH of said aqueous alkaline processing composition and which, after at least the initial stages of processing, is converted to its colorless form by reducing the environmental pH, for example, by including an acidreacting layer as part of the film unit. The concentrations of the light-reflecting pigment and light-absorbing optical filter agent required to provide adequate protection of the photosensitive layer(s) will vary with the process being performed and the anticipated conditions, e.g., light intensity, dark time, etc. Preferably, the concentrations of these materials are such that the processing composition layer containing the pigment and optical filter agent will have a transmission density of at least about 6 but a reflection density not greater than about 1.

Various pH-sensitive dyes have been disclosed as light-absorbing optical filter agents for protecting a selectively exposed photosensitive material from post-exposure fogging in the presence of extraneous incident light. Examples of pH-sensitive dyes that have been found particularly useful are the phthaleins, i.e., the phthalide and naphthalide dyes derived from indoles disclosed in U.S. Pat. No. 3,702,244 issued Nov. 7, 1972 to Stanley M. Bloom, Alan L. Borror, Paul S. Huyffer and Paul T. MacGregor, and the phthalide and naphthalide dyes derived from phenols and 1-naphthols disclosed in U.S. Pat. No. 3,702,245 issued Nov. 7, 1972 to Myron S. Simon and David P. Waller. As discussed in the latter patent, phenol and 1-naphthol phthaleins especially useful for photographic processes employing highly alkaline media are those possessing a hydrogen-bonding group, for example, a carboxy group ortho to the p-hydroxy group of the phenol or naphthol radicals. These phthaleins also may contain other substituents, and as discussed in column 7, lines 40 to 64, the hydrogen-bonding or other substituent may comprise a fused ring. For example, the phenol or naphthol radicals may contain as a fused substituent, a fused cycloaliphatic or aromatic ring usually having 5 or 6 members which ring may be carbocyclic or heterocyclic and unsubstituted or substituted. As an illustration, fused rings may be employed to give a hydrogen-bonded radical such as 8-hydroxy-5-quinolyl, 5-hydroxy-4-azaphenanthren-8yl and a phenanthrol radical substituted in the peri position with, e.g., hydroxy. As discussed in these and other patents, the 1-naphthol or phenol phthaleins generally are used in combination with the indole phthaleins where it is desired to provide protection from post-exposure fogging throughout the visible spectrum.

U.S. Pat. No. 4,456,674 issued June 26, 1984 to Leon D. Cerankowski, Gary S. LaPointe and Neil C. Mattucci discloses enhanced opacification systems employing metal cations for complexing with phthalein optical filter agents and in one embodiment discloses the use of an alkali earth metal salt to increase the light-absorbing ability of a carboxynaphthol phthalein within the layer of processing composition.

SUMMARY OF THE INVENTION

According to the present invention, it has been found that certain substituted phenanthrol/o-carboxynaphtol phthaleins, namely, o-alkylphenanthrol/o-carboxynaphthol phthaleins provide enhanced protection against post-exposure fogging in the red and near infrared region of the visible spectrum. In comparison to unsubstituted phenanthrol/o-carboxynaphthol phthaleins and di-(o-carboxynaphthol) phthaleins, the subject phthaleins possess a broader absorption spectrum that extends into the far red and near infrared and absorb incident radiation more strongly at the longer wavelengths. Also, they exhibit substantial absorption in the blue and green regions, better alkaline stability and less interaction with other reagents that may be present in the photographic system, particularly, quaternary compounds. Because of these improved properties, the subject phthalein optical filter agents allow the use of thinner layers of pigmented reagent and/or more efficient use, i.e., lesser concentrations of optical filter agent without requiring the addition of metal salts or other material to provide added protection.

It is, therefore, the primary object of the present invention to provide diffusion transfer photographic products and processes employing as the processing composition, an aqueous alkaline solution of a light-reflecting pigment and an o-alkylphenanthrol/o-carboxynaphthol phthalein as at least one light-absorbing pH-sensitive optical filter agent.

It is another object of the present invention to provide photographic products and processes of the foregoing type wherein the processing composition additionally includes a light-absorbing, pH-sensitive indole phthalein optical filter agent.

It is a further object of the present invention to provide o-alkylphenanthrol/o-carboxynaphthol phthaleins useful as light-absorbing, pH-sensitive optical filter agents.

Other objects of this invention will in part be obvious and will in part appear hereinafter.

The invention accordingly comprises the processes involving the several steps and the relation and order of one or more of such steps with respect to each of the others, and the products possessing the features, properties and relation of elements which are exemplified in the following detailed disclosure, and the scope of the application of which will be indicated in the claims.

For a fuller understanding of the nature and objects of the invention, reference should be had to the following detailed description taken in conjunction with the accompanying drawings.

DETAILED DESCRIPTION OF THE INVENTION

Figure 1:
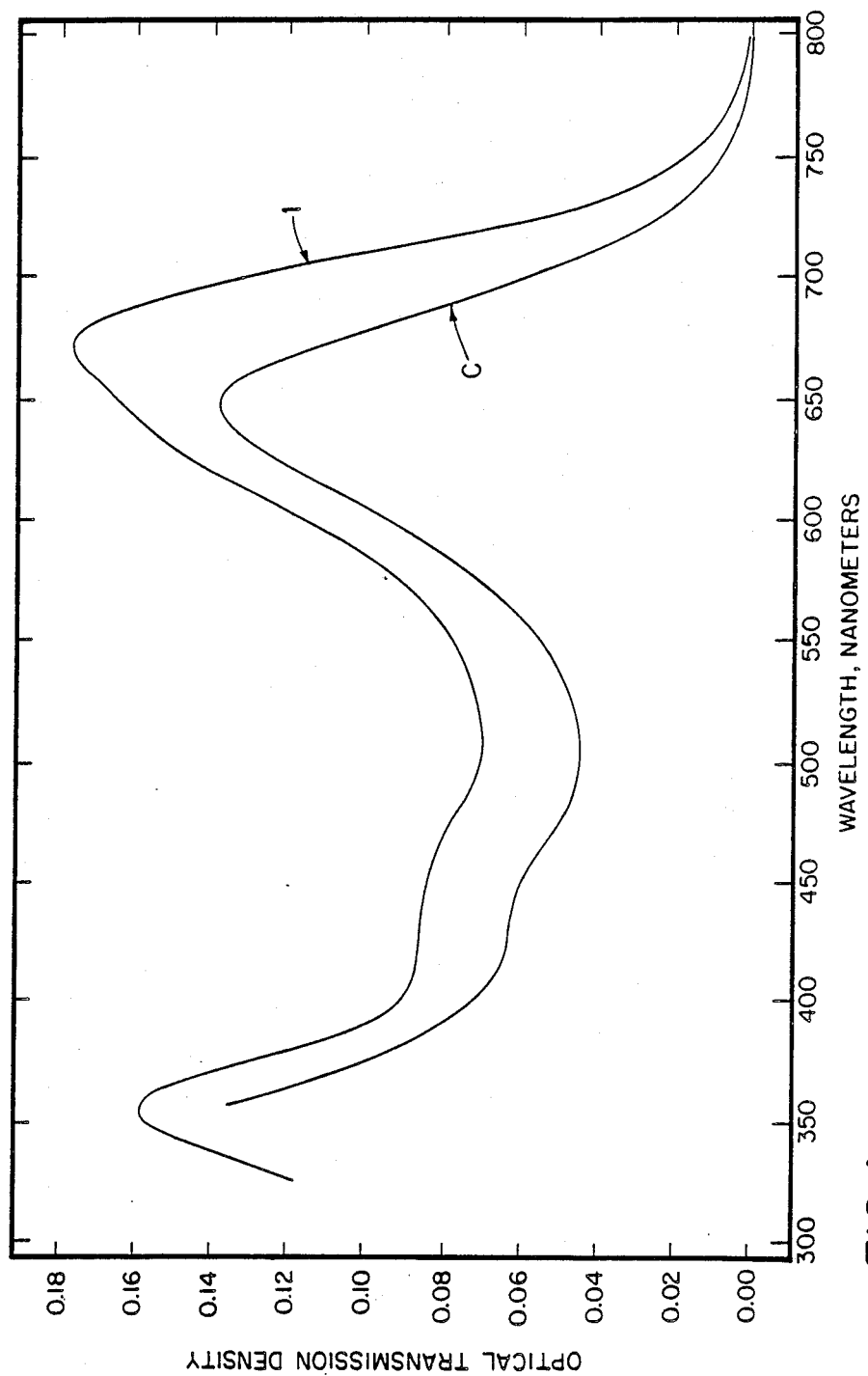
FIGS. 1 and 2 are graphic illustrations comparing the spectral absorption characteristics of the phthalein optical filter agent of Example 1 of the present invention designated Curve 1 with the spectral absorption characteristics of a di-(o-carboxynaphthol) phthalein optical filter agent (Curve C) and also with an unsubstituted phenanthrol/o-carboxynaphthol phthalein optical filter agent (Curve C'). These curves represent the optical transmission density, i.e., the absorbance of the respective optical filter agents measured over the wavelength range of 350 nm to 800 nm in aqueous alkaline solution.

As noted above, it has been found that enhanced opacification of a pigmented processing composition layer and, particularly, added protection in the red and near infrared region of the visible spectrum and also in the blue and green region can be achieved by employing certain o-alkylphenanthrol/o-carboxynaphthol phthaleins as the light-absorbing, pH-sensitive optical filter agent for the longer wavelength region of the visible spectrum. As used herein the term "phthalein" is intended to include both phthalides and naphthalides. These phthaleins may be represented by the formula

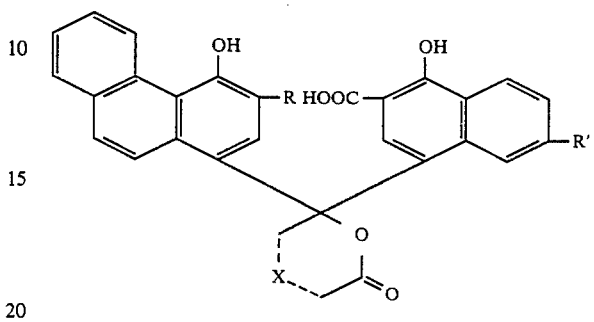

wherein R is alkyl having 1 to 6 carbon atoms, R' is alkoxy having at least 12 carbon atoms and X represents the carbon atoms necessary to complete phthalide or naphthalide. The respective phthalide and naphthalide moieties are represented by the following formulae:

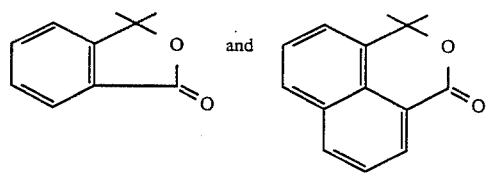

Preferably, X completes naphthalide.

Illustrative R substituents include branched or straight chain alkyl having 1 to 6 carbon atoms such as methyl, ethyl, isopropyl, n-butyl, isobutyl, pentyl and hexyl. Preferably, R is methyl. Illustrative R' substituents include branched or straight chain alkoxy having at least 12 carbon atoms and usually having 12 to 24 carbon atoms such as hexadecyloxy, octadecyloxy, eicosanyloxy and docosanyloxy.

The subject phthaleins may be prepared using any of the various methods previously disclosed for synthesizing phthalides and naphthalides such as that described in U.S. Pat. No. 3,931,228. A preferred method is described in U.S. Pat. No. 3,869,473 and comprises reacting a 3-acyloxy-3-(3'-lower carboalkoxy4'-hydroxy-1'-naphthyl) naphthalide and the select phenanthrol in the presence of base such as pyridine to form the corresponding dye precursor which is then hydrolyzed to yield the corresponding dye product. The 3-acyloxy compounds employed in the above-described method are known and may be prepared according to the procedure disclosed in U.S. Pat. No. 3,806,523.

The following examples are given to illustrate the invention and are not intended to limit the scope thereof.

EXAMPLE 1

Preparation of the compound having the formula

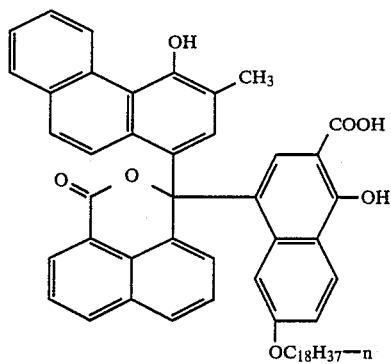

(1) To 110 ml of dry benzene was added 10.0 g of 3-acetoxy-3-(3'-carbomethoxy-4'-hydroxy-7'-n-octadecyloxy-1'-naphthyl) naphthalide and 2.9 g of 3-methyl-4phenanthrol. This mixture was stirred under nitrogen, 7.0 ml of benzene containing pyridine (0.3 ml of pyridine per 50 ml of benzene) was added and the resulting mixture was refluxed under nitrogen for 9 hours then allowed to stir overnight at room temperature. The light amber reaction mixture was filtered to remove a small amount of tan solids and the filtrate evaporated to an oil. A large excess of hexanes was added to the oil and the mixture cooled in an ice water bath. The hexanes were decanted from the oil that separated and the oil was triturated with fresh hexanes to give solids. The solids were collected by filtration, washed and then heated with fresh hexanes. After cooling, the solids were filtered and dried under vacuum for one hour at 45° C. to yield 7.76 g of the methyl ester dye precursor as an off-white solid. M.P. 205°–207° C.

(2) 7.7 g of the methyl ester dye precursor were suspended in 150 ml of isopropanol under nitrogen and 150 ml of slightly warm 10% aqueous sodium hydroxide solution was added giving a blue-green mixture. After stirring under nitrogen at room temperature and for one hour at 40° C., the cooled mixture was poured into 800 ml of distilled water containing 26 ml of glacial acetic acid and 38 ml of conc. hydrochloric acid. The light tan solid that precipitated was filtered, washed with 500 ml of distilled water and air dried for two hours followed by vacuum drying at 40° C. for one hour. The solid was dissolved in methylene chloride. The white solid that precipitated (2.0 g) was collected by filtration and combined with the additional solid recovered from the cooled filtrate. The combined solids were vacuum dried for 3 hours at 50° C. to yield 4.29 g of the title compound. M/e 845; M.P. 205°–207° C.;λmax 673 (17,700) in 1N KOH.

The 3-acetoxy-3-[3'-carbomethoxy-4'-hydroxy-7'-n-octadecyloxy-1'-naphthyl) naphthalide used in Example 1 above was synthesized as follows:

(a) 13.8 g of naphthalic anhydride was suspended in 100 mls of o-dichlorobenzene and 15.0 g of phosphorous pentachloride was added. The mixture was heated at 150°–157° C. under nitrogen for 6 hours, the reaction mixture was cooled in an ice water bath to 10° C. and 9.3 g of anhydrous aluminum chloride was added in small increments over a 30 minute period giving a yellow slurry. The slurry was cooled to 8° C. and 32.8 g of solid methyl 1-hydroxy-6-octadecyloxy-2-naphthoate was added in small increments over a 30 minute period to give a dark blue slurry. This slurry was stirred under nitrogen at room temperature over the weekend. Then 20 ml of o-dichlorobenzene was added and the slurry was poured on crushed ice, followed by heating on a steam bath at 65°–75 ° C. for 30 minutes to give a tan suspension. The suspension was cooled in an ice water bath and the water layer was separated. The organic portion was washed again with ice cold water, then diluted with 1.5 liters of hexanes and allowed to stand in an ice bath for 2 hours. The tan solids were filtered. The solids were recrystallized from approximately 750 mls of acetonitrite, collected, washed with hexanes and dried overnight under vacuum at 60° C. to give 30.2 g of 3-hydroxy-3-(3'-carbomethoxy-4'-hydroxy7'-n-octadecyloxy-1'-naphthyl) naphthalide as a tan solid. M.P. 108°-110° C.; λmax 262 (E =45,300) methanol.

(b) To 15.0 g of 3-hydroxy-3-(3'-carbomethoxy-4'-hydroxy-7'-n-octadecyloxy1'-naphthyl) naphthalide was added 23.5 ml acetic acid and 16.9 ml acetic anhydride. The resulting paste was heated at about 110°–115° C. under nitrogen to give a clear, amber-colored reaction mixture. After 2.5 hours, the cooled mixture was diluted with 80 ml of 1:3 hexane-toluene, cooled in an ice water bath, and filtered to collect the solids. The solids were washed with 50:50 toluene-hexanes, then with hexanes and dried under vacuum for 80 minutes to give 10.15 g of 3-acetoxy-3-(3'-carbomethoxy-4'-hydroxy7'-n-octadecyloxy-1'-naphthyl) naphthalide as a white solid. M.P. 132°–135° C.

The 3-methyl-4-phenanthrol employed in Example 1 above was synthesized as set out in the following reaction scheme:

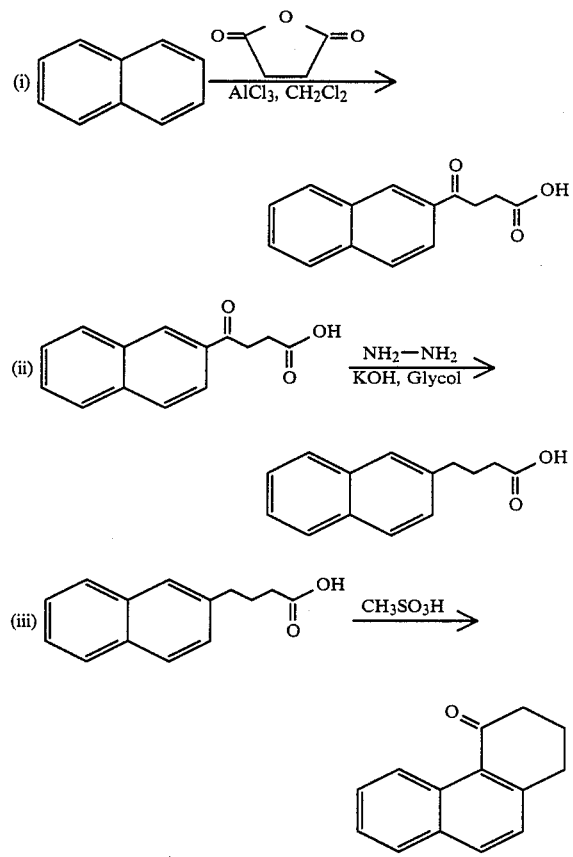

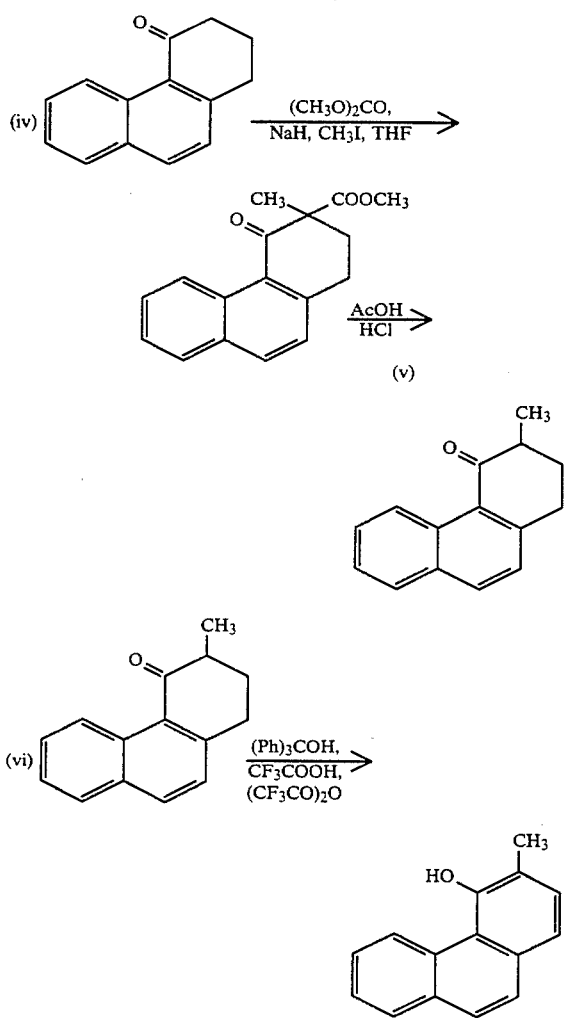

To 900 ml of dichloromethane contained in a 3 liter, 3-neck flask equipped with a mechanical stirrer, drying tube and thermometer and surrounded by an ice water bath was added 290.0 g (2.26 moles) naphthalene. To the stirred suspension was added 145.2 g (1.44 moles) of succinic anhydride. A total of 400 g of aluminum chloride was then added in small increments over the next 4½ hours while stirring and cooling in an ice water bath. The resulting amber brown-yellow reaction mixture was stirred at room temperature overnight. Next morning it was poured on crushed ice and acidified with conc. hydrochloric acid. The aqueous portion was decanted and the organic layer was filtered to collect white solids. The solids were washed with dichloromethane containing 20% hexanes and slurried in 700 ml of boiling ethyl acetate. After cooling in a cold water bath, the solids were collected by filtration and washed with fresh ethyl acetate. Then the solids were recrystallized from 500 ml of glacial acetic acid and dried under vacuum to give 195.0 g (59.4% yield) of 4-(2-naphthyl)4-oxobutyric acid as an off-white solid. M.P. 171°–175° C.; M/e 229; λmax 282 nm (7,260) in ethanol.

(ii) To 300 ml of triethylene glycol contained in a 1-liter, 3-neck flask equipped with a magnetic stirrer, thermometer and take-off condenser was added 77.0 g (0.34 mole) of 4-(2-naphthyl)-4-oxobutyric acid, 61.2 g (1.09 moles) potassium hydroxide pellets and 45.44 ml of hydrazine monohydrate. The reaction mixture was heated up to 100°–110° C. with stirring and held there for 90 minutes. The temperature was gradually increased to 195° C. over 4 hours. Strong gas evolution commenced at about 130° C. with some distillate coming over above 140° C. The reaction mixture was allowed to cool and then stirred at room temperature overnight. Next morning the reaction mixture was diluted with ice water and while cooling in ice was acidified with conc. hydrochloric acid. The white solids were collected by filtration, washed with warm water and air-dried to yield 69.0 g (94.9% by weight yield) of γ-(2-naphthyl) butyric acid. M.P. 96°–99° C.; M/e 214; λmax 276 (5,580) ethanol.

(iii) To 300 ml of methane-sulfonic acid contained in a 1 liter, 3-neck flask equipped with thermometer, drying tube and magnetic stirring bar was added 82.0 g (0.38 mole) of γ-(2-naphthyl)butyric acid as prepared above and the reaction mixture was heated at 90°–95° C. for one hour with vigorous stirring. The yellow reaction mixture was cooled, poured on crushed ice and extracted with two 350 ml portions of ethyl acetate. The combined organic portions were washed with 5% aqueous sodium hydroxide, water, dried over anhydrous sodium sulfate and then treated with some silica gel powder and Norit A charcoal before filtering. Upon removing the solvent an off-white solid was obtained. Recrystallization from 375 ml of hexane containing 7–10 ml of chloroform gave an oil that solidified to yield 55.0 g (73.3% by weight) of 1,2,3,4-tetrahydro-4-phenanthrone as an off-white solid. M.P. 64°–66° C.; λmax 312 nm (7,510) ethanol; T.L.C. CH₂Cl₂. R$_f$=.7.

(iv) In a 1 liter, 3-neck flask equipped with magnetic stirrer and reflux condenser (protected with a drying tube) 43.7 g (0.223 mole) of 1,2,3,4-tetrahydro-4-phenanthrone was dissolved in 225 ml of tetrahydrofuran, and 14.0 g of 59.3% sodium hydride in oil and 1.2 g of 25% potassium hydride in oil were added. The reaction mixture was refluxed for 45 minutes, cooled to room temperature, and then 60 ml of dimethyl carbonate was added all at once with vigorous stirring. The temperature gradually rose to reflux and refluxing was continued for 2½ hours. The reaction mixture was cooled in an ice water bath, and 14.0 g of 59.3% sodium hydride in oil was added to the slurry which was stirred vigorously. Excess iodomethane (40 ml) was then added in small increments over a 30 minute period. Hydrogen evolution occurred. The mixture was stirred cold for another 30 minutes and at gentle reflux for 90 minutes. The reaction mixture was filtered and the filtrate evaporated to give tan solids. Recrystallization of the tan solids from 220 ml methanol containing 25 ml water gave 48.6 g (81.25% by weight yield) of 3-carboxymethyl-3-methyl-1,2,3,4-tetrahydro-4phenanthrone as a light gray, crystalline solid. M.P. 80°–83 ° C., M/e 269, λmax 313 (6,700) methanol.

(v) In a 1-neck 500 ml flask topped with a reflux condenser 250 ml of acetic acid, 50 ml of conc. hydrochloric acid and 50 ml of water were mixed together. To this mixture was added 27.7 g (0.0846 mole) of 3-carboxymethyl-3methyl-1,2,3,4-tetrahydro-4-phenanthron and the reaction mixture was refluxed for 3½ hours under nitrogen. The mixture was diluted with 300 ml water and cooled in the refrigerator overnight. Next morning offwhite solids were collected by filtration, washed with water and dried under vacuum to give 16.9 g (95.02% by weight yield) of 3-methyl-1,2,3,4-tetrahydro-4-phenanthrone as an off-white solid. M.P. 61°–63° C.; M/e 211; λmax 309 (6,970) methanol.

(vi) In a 500 ml 3-neck flask equipped with magnetic stirrer and reflux condenser with nitrogen inlet, 66 ml of trifluoroacetic acid and 88 ml of trifluoroacetic anhydride were mixed together cautiously. The mixture was stirred under nitrogen and 54.6 g (0.21 mole) of 97% triphenylmethanol was added in increments over a 30 minute period giving an intense yellow-green solution. Heat was liberated. The reaction mixture was refluxed for one hour, cooled and 22.0 g (0.105 mole) of 3-methyl-1,2,3,4-tetrahydrophenanthrone as prepared above was added all at once, followed by refluxing under nitrogen for 21 hours. The amber mixture was cooled in an ice water bath and filtered to remove the solids. The filtrate was poured on crushed ice and the light tan precipitate was collected, washed with water and air-dried overnight. The solids were extracted with several portions of hexanes at room temperature to take up the 4-phenanthrol trifluoroacetate. The hexanes were concentrated to 400 ml, cooled in a freezer, then filtered. The filtrate was concentrated under vacuum to an oil. 40 ml of degassed 10% aqueous sodium hydroxide (containing a trace amount of sodium hydrosulfite) was added to the oil, followed by 110 ml of methanol. Nitrogen was passed through the mixture with stirring for one hour at room temperature. The mixture was filtered, and while cooling in an ice water bath, the filtrate was acidified with dilute hydrochloric acid to give a light tan precipitate. The precipitate was collected by filtration, washed with water and dried under vacuum to give 17.9 g (79.13% by weight) of 3-methyl-4-phenanthrol as a tan solid. M/e 208; M.P. 88°–92° C.; λmax 275 (16,200) methanol.

EXAMPLE 2

Preparation of the compound having the formula

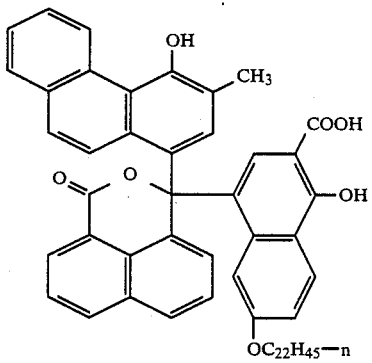

The title compound was prepared according to the procedure given in Example 1 using 3-acetoxy-3-(3'-carbomethoxy-4'-hydroxy-7'-n-docasanyloxy-1'-naphthyl) naphthalide for reaction with 3-methyl-3-methyl-4-phenanthrol.

EXAMPLE 3

Preparation of the compound having the formula

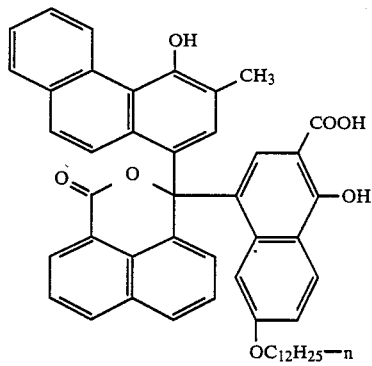

The title compound was prepared according to the procedure given in Example 1 using 3-acetoxy-3-(3'-carbomethoxy-4'-hydroxy-7'-dodecanyloxy-1'naphthyl) naphthalide for reaction with 3-methyl-4-phenanthrol.

Example 4

Preparation of the compound having the formula

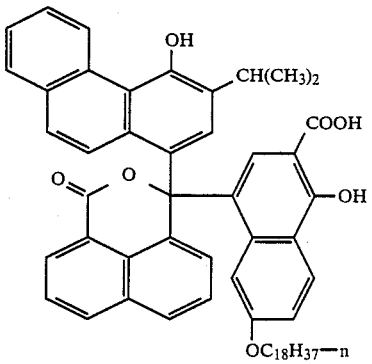

The title compound was prepared according to the procedure given in Example 1 above using 3-isopropyl-4-phenanthrol for reaction, with 3-acetoxy-3-(3. '-carbomethoxy-4'-hydroxy-7'-octadecyloxy-1'-naphthyl) naphthalide.

As noted above, the present invention is particularly adapted for facilitating processing outside of a camera of diffusion transfer units which are maintained as a permanent integral laminate after processing, the final transfer image being viewed through one face of the laminate. In such film units a light-reflecting layer is disposed between the developed photosensitive layers and the layer carrying the transfer dye image. These essential layers preferably are confined between a pair of dimensionally stable outer supports, at least one of which is transparent to permit viewing of the transfer dye image by reflection against the background provided by the reflecting layer.

Image dye-providing materials which may be employed generally may be characterized as either (1) initially soluble or diffusible in the processing composition but are selectively rendered non-diffusible in an imagewise pattern as a function of development; or (2) initially insoluble or non-diffusible in the processing composition but which are selectively rendered diffusible or provide a diffusible product in an imagewise distribution as a function of development. These materials may be complete dyes or dye intermediates, e.g., color couplers. The requisite differential in mobility or solubility may, for example, be obtained by a chemical action such as a redox reaction, a coupling reaction or a silver ion assisted cleavage reaction.

Examples of initially soluble or diffusible materials and their application in color diffusion transfer processes are disclosed, for example, in U.S. Pat. Nos. 2,968,554; 2,983,606; 3,087,817; 3,185,567; 3,230,082; 3,345,163; and 3,443,943. Examples of initially non-diffusible materials and their use in color transfer systems are disclosed in U.S. Pat. Nos. 3,185,567; 3,443,939; 3,443,940; 3,227,550; 3,227,552 and 4,076,529. Both types of image dye-providing substances and film units useful therewith also are discussed in the aforementioned U.S. Pat. No. 3,647,437 to which reference may be made.

A particularly useful system for forming color images by diffusion transfer is that described in U.S. Pat. No. 2,983,606, employing dye developers (dyes which are also silver halide developing agents) as the image dye-providing materials. In such systems, a photosensitive element comprising at least one silver halide layer having a dye developer associated therewith (in the same or in an adjacent layer) is developed by applying an aqueous alkaline processing composition. Development of exposed silver halide results in oxidation of the dye developer to provide an oxidation product which is appreciably less diffusible than the unreacted dye developer, thereby providing an imagewise distribution of diffusible dye developer in terms of unexposed areas of the silver halide layer, which imagewise distribution is then transferred, at least in part, by diffusion, to a dyeable stratum to impart thereto a positive dye transfer image.

Another system that is particularly useful for forming color images by diffusion transfer is that described in U.S. Pat. No. 4,740,448, which uses the aforementioned dye developer chemistry to form at least one color record and the image dye-releasing thiazolidine chemistry of U.S. Pat. No. 3,719,489 to form at least one of the other color records.

In such color diffusion transfer systems, color transfer images are obtained by exposing a photosensitive element, sometimes referred to as a "negative component", comprising at least a light-sensitive layer, e.g., a gelatino silver halide emulsion layer, having an image dye-providing material associated therewith in the same or in an adjacent layer, to form a developable image; developing this exposed element with a processing composition to form an imagewise distribution of a diffusible image dye-providing material; and transferring this imagewise distribution, at least in part, by diffusion, to a superposed imagereceiving layer, sometimes referred to as a "positive component", comprising at least a dyeable stratum to provide a color transfer image. The negative and positive components initially may be carried on separate supports which are brought together during processing and thereafter retained together as the final integral negative-positive reflection print, or they may initially comprise a unitary structure, e.g., integral negative-positive film units of the type described in aforementioned U.S. Pat. No. 3,415,644 wherein the negative and positive components are physically retained together in superposed relationship prior to, during and after image formation. (Procedures for forming such film units wherein the positive and negative components are temporarily laminated together prior to exposure are described, for example, in U.S. Pat. No. 3,652,281 to Albert J. Bachelder and Frederick J. Binda and in U.S. Pat. No. 3,652,282 to Edwin H. Land, both issued Mar. 28, 1972.) In either instance, the positive component is not removed from the negative component for viewing purposes. These components may be laminated together or otherwise secured together in physical juxtaposition.

Film units intended to provide multicolor images comprise two or more selectively sensitized silver halide layers each having associated therewith an appropriate image dye-providing material providing an image dye having spectral absorption characteristics substantially complementary to the light by which the associated silver halide is exposed. The most commonly employed negative components for forming multicolor images are of the tripack structure and contain blue-, green- and red-sensitive silver halide layers each having associated therewith in the same or in a contiguous layer a yellow, a magenta and a cyan image dye-providing material, respectively. Interlayers or spacer layers may be provided between the respective silver halide layers and associated image dye-providing materials or between other layers. Indeed, a light-reflecting spacer layer disposed between a silver halide layer and the associated layer of image dye-providing material may be used to increase effective film speed as a result of the reflection of light back to the silver halide. Particularly suitable light-reflecting spacer layers comprise a light-reflecting pigment dispersed with inert polymeric particles which are substantially non-swelling in alkali and substantially non-film-forming. Such layers form the subject matter of published European Patent Application No. 0066341 published Dec. 8, 1982.

In addition to the aforementioned layers, such film units further include means for providing a reflecting layer between the dyeable stratum and the negative component in order to mask effectively the silver image or images formed as a function of development of the silver halide layer or layers and also to mask image dye-providing material which is not transferred, thereby providing a background, preferably white, for viewing the color image formed in the dyeable stratum, without separation, by reflected light. Preferably, this reflecting layer is provided by including the reflecting agent in the processing composition. The dye transfer image is then viewable against the reflecting layer through a dimensionally stable protective layer or support. As noted above, most preferably another dimensionally stable layer or support is positioned on the opposed surface of the essential layers so that the aforementioned essential layers are between a pair of dimensionally stable layers or support members, one of which is transparent to permit viewing therethrough of the color transfer image. A rupturable container of known description contains the requisite processing composition and is adapted upon application of pressure to release its contents for development of the exposed film unit, e.g., by distributing the processing composition in a substantially uniform layer between the negative and positive components.

The dye developers (or other image dye-providing substances) are preferably selected for their ability to provide colors that are useful in carrying out subtractive color photography, that is, the previously mentioned cyan, magenta and yellow. They may be incorporated in the respective silver halide emulsion or, in the preferred embodiment, in a separate layer behind the respective silver halide emulsion. Thus a dye developer may, for example, be in a coating or layer behind the respective silver halide emulsion and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Dye developers, as noted above, are compounds which contain the chromophoric system of a dye and also a silver halide developing function. By "a silver halide developing function" is meant a grouping adapted to develop exposed silver halide. A preferred silver halide development function is a hydroquinonyl group. Other suitable developing functions include orthodihydroxyphenyl and ortho- and para-amino substituted hydroxyphenyl groups. In general, the development function includes a benzenoid developing function, that is, an aromatic developing group which forms quinonoid or quinone substances when oxidized.

The image-receiving layer may comprise any of the materials known in the art, such as polyvinyl alcohol, gelatin, etc., preferably containing a mordant for the transferred image dye(s). If the color of the transferred image dye(s) is affected by changes in pH, the pH of the image layer may be adjusted to provide a pH affording the desired color.

In the various color diffusion transfer systems which have previously been described and which employ an aqueous alkaline processing fluid, it is well known to employ an acid-reacting reagent in a layer of the film unit to lower the environmental pH following substantial dye transfer in order to increase the image stability and/or to adjust the pH from the first pH at which the image dyes are diffusible to a second (lower) pH at which they are not. For example, the previously mentioned U.S. Pat. No. 3,415,644 discloses systems wherein the desired pH reduction may be effected by providing a polymeric acid layer adjacent the dyeable stratum. These polymeric acids may be polymers which contain acid groups, e.g., carboxylic acid and sulfonic acid groups, which are capable of forming salts with alkali; or potentially acid-yielding groups such as anhydrides or lactones. Preferably the acid polymer contains free carboxyl groups. Alternatively, the acid-reacting reagent may be in a layer adjacent the silver halide most distant from the image-receiving layer, as disclosed in U.S. Pat. No. 3,573,043 issued Mar. 30, 1971 to Edwin H. Land. Another system for providing an acid-reacting reagent is disclosed in U.S. Pat. No. 3,576,625 issued Apr. 27, 1971 to Edwin H. Land.

An inert interlayer or spacer layer may be used in association with the polymeric acid layer to control or "time" the pH reduction so that it is not premature and interfere with the development process. Suitable spacer or "timing" layers useful for this purpose are described with particularity in U.S. Pat. Nos. 3,362,819; 3,419,389; 3,421,893; 3,455,686; and 3,575,701.

As is now well known and illustrated, for example, in the previously cited patents, the liquid processing composition referred to for effecting multicolor diffusion transfer processes comprises at least an aqueous solution of an alkaline material and possesses a pH of at least 12. Preferably, the alkaline material employed in the subject invention, is an alkali metal hydroxide.

The processing composition also preferably includes a viscosity-imparting reagent constituting a film-forming material of the type which, when the composition is spread and dried, forms a relatively firm and relatively stable film. This reagent may be a cellulosic polymer, for example, hydroxyethyl cellulose or sodium carboxymethyl cellulose; an oxime polymer, for example, polydiacetone acrylamide oxime; or other alkali-stable high molecular weight polymer. The viscosity-imparting reagent is preferably contained in the processing composition in such suitable quantities as to impart to the composition a viscosity in excess of 100 cps. at a temperature of approximately 24° C. and preferably in the order of 100,000 cps. to 200,000 cps. at that temperature.

As mentioned previously, a light-absorbing pH sensitive optical filter agent which absorbs in the shorter wavelength range of the visible spectrum, usually, an indole phthalein is used in combination with the subject phthaleins to provide further protection throughout the visible spectrum. As used herein, the term "indole phthalein" is intended to include both 3,3-di(indol-3-yl) phthalides and 3,3-di(indol-3-yl) naphthalides such as the phthaleins disclosed in aforementioned U.S. Pat. No. 3,702,244. Preferred indole phthaleins are those forming the subject matter of U.S. Pat. No. 4,615,966.

The pH-sensitive phthalein dye(s) employed as the light-absorbing optical filter agents preferably are initially contained in the processing composition in their colored form together with the light-reflecting material, for example, titanium dioxide. The concentration of phthalein dye is selected to provide the optical transmission density required, in combination with the other layers intermediate the silver halide emulsion layer(s) and the incident radiation, to prevent nonimagewise exposure, i.e., fogging by incident actinic light during performance of the particular photographic process. The transmission density and the concentration of phthalein dye necessary to provide the requisite protection from incident light may be readily determined for any photographic process by routine experimentation, as a function of film speed or sensitivity, thickness of opacification layer, processing time, anticipated incident light intensity, etc., as described in said U.S. Pat. No. 3,647,437. It will be recognized that a particular transmission density may not be required for all portions of the spectrum, lesser density being sufficient in wavelength regions corresponding to lesser sensitivities of the particular photosensitive material. As indicated above, it will be recognized that a mixture of phthalein dyes may be used to obtain absorption in all critical areas of the visible and near-visible by which the silver halide emulsions being used are exposable.

Where the light-absorbing phthalein optical filter agent is present in the processing composition, it is advantageous to utilize an image-receiving component having a surface layer adapted to decolorize the optical filter agent adjacent the interface between said component and the layer of processing composition. Suitable decolorizing layers are described in U.S. Pat. No. 4,298,674 of Edwin H. Land, Leon D. Cerankowski and Neil C. Mattucci, in U.S. Pat. No. 4,294,907 of Irena Bronstein-Bonte, Edward P. Lindholm and Lloyd D. Taylor and in U.S. Pat. 4,367,277 of Charles K. Chiklis and Neil C. Mattucci.

Figure 2:
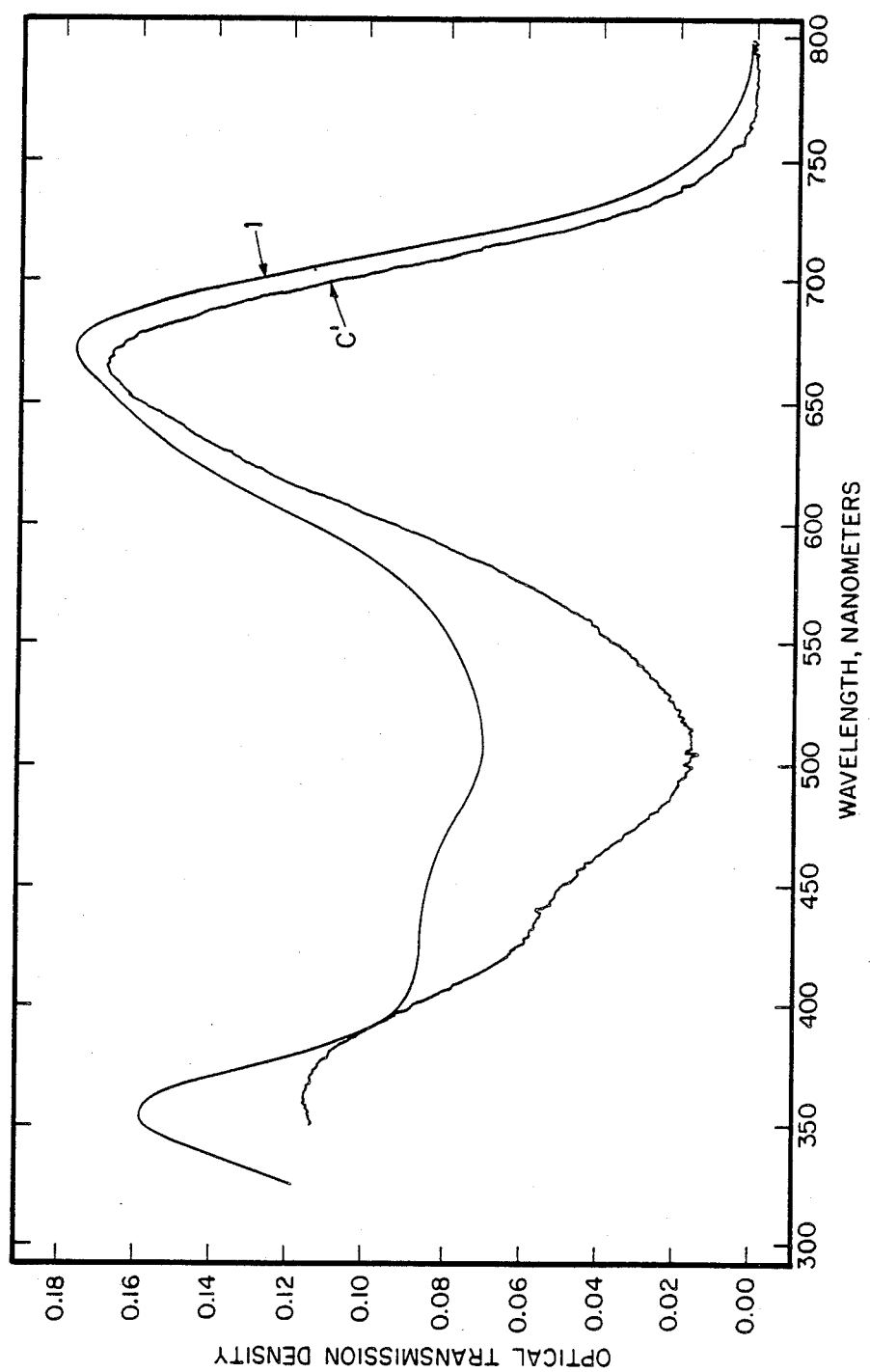

To further illustrate the present invention, the optical transmission density of the compound of Example 1 at a concentration of $1 \times 10^{-4}$ in 1N aqueous potassium hydroxide solution was measured spectrophotometrically over the wavelength range of 350 nm to 800 nm. The resulting curve designated Curve 1 is shown in FIG. 1. As a comparison, the transmission density of a di-(o-carboxynaphthol) phthalein (Compound C) was measured in the same manner and at the same concentration in 1N aqueous potassium hydroxide solution. The resulting curve is designated Curve C in FIG. 1. FIG. 2 represents a comparison in optical transmission density between the compound of Example 1 and an unsubstituted phenanthrol/o-carboxynaphthol phthalein (Compound C') as measured spectrophotometrically at a concentration of $1 \times 10^{-4}$ in 1N aqueous potassium hydroxide solution.

Unsubstituted phenanthrol/o-carboxynaphthol phthaleins such as Compound C' and their use as optical filter agents form the subject matter of copending U.S. Pat. Application Ser. No. 252,661 of Myron S. Simon filed concurrently herewith.

Figure 3:
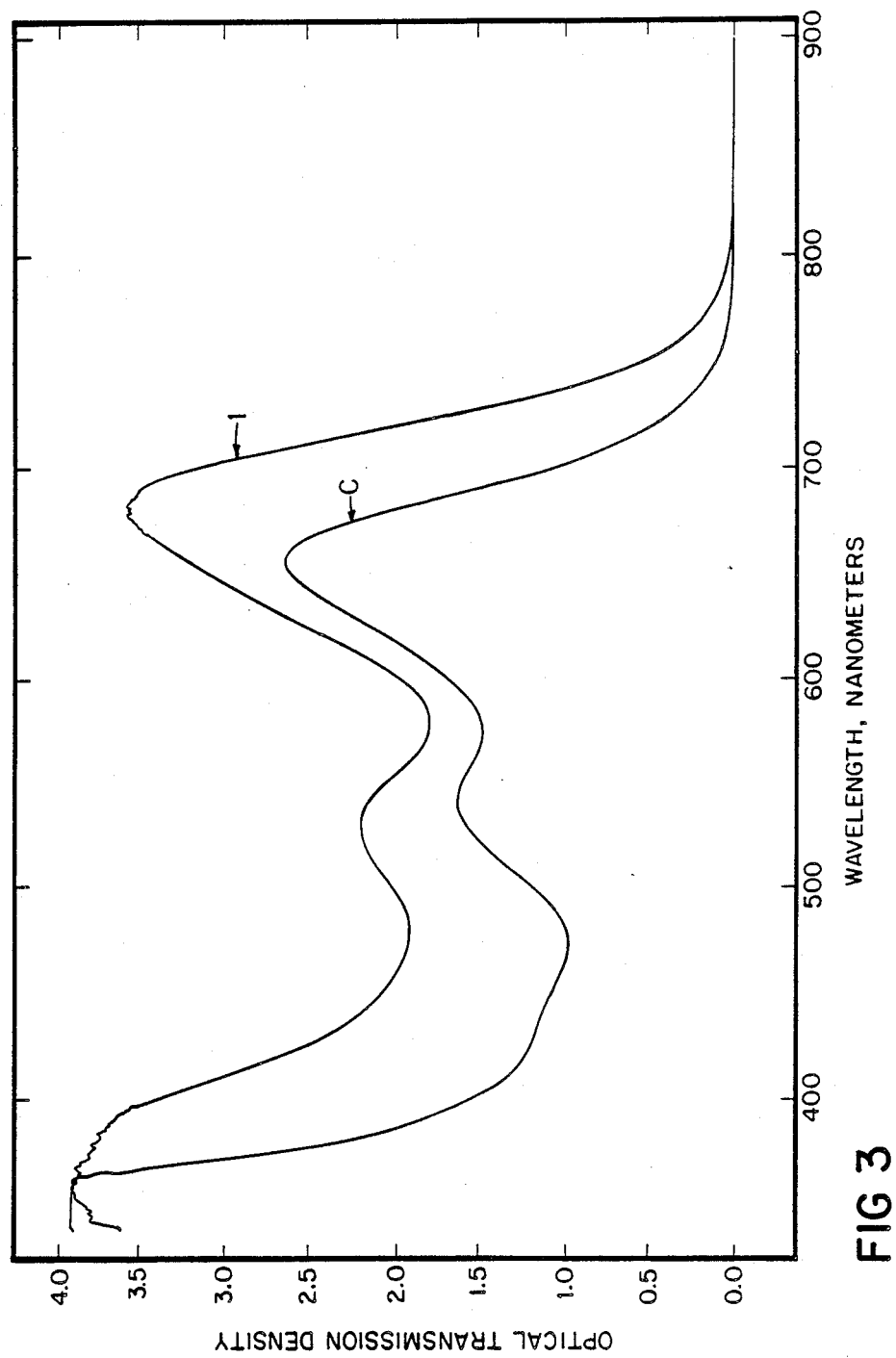
FIG. 3 is a graphic illustration showing the absorption characteristics of aqueous alkaline processing compositions over the wavelength range of about 350 nm to 900 nm wherein the compositions are the same except for the phthalein optical filter agent. Curve 1 represents the optical transmission density obtained using the compound of Example 1 of the present invention, and Curve C represents the optical transmission density obtained using a di(o-carboxynaphthol) phthalein.

The increased protection in the red and near infrared region provided by he subject phthaleins is further illustrated by the absorption spectra in FIG. 3 wherein Curve 1 represents a processing composition containing the compound of Example 1 and Curve C represents a processing composition containing Compound C. These curves represent the optical transmission densities for aqueous alkaline processing compositions measured spectrophotometrically without dilution in a 0.005 cm cell after removal of titania pigment by centrifugation. The processing compositions were identical except for the phthalein optical filter agent used as the longer wavelength absorber. Besides the respective longer wavelength absorbers, the processing compositions comprised a viscous aqueous solution of an alkali metal hydroxide containing the indole phthalein of the following formula as the optical filter agent for absorbing in the shorter wavelength range of the visible spectrum.

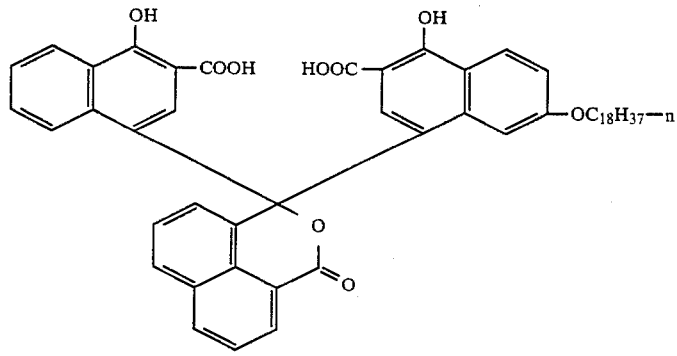

3-(3'-carboxy-4'hydroxy-1'-naphthyl)-3-(3''-carboxy-4''-hydroxy-7''-octadecyloxy-1''-naphthyl)naphthalide Compound C

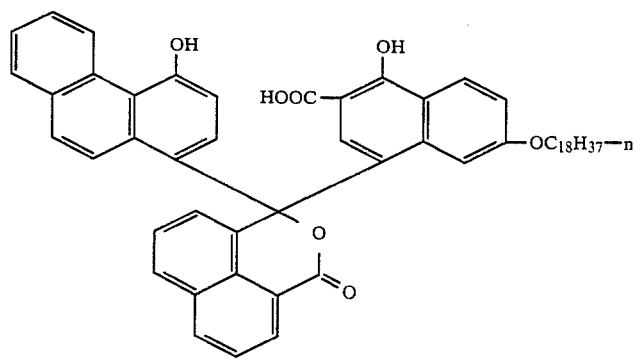

3-(4'-hydroxy-1'-phenanthryl)-3-(3''-carboxy-4''-hydroxy-7''-octadecyloxy-1''-naphthyl)naphthalide.

Compound C'

As can be seen from reference to FIGS. 1 and 2, the o-alkyl phenanthrol/o-carboxynaphthol phthaleins of the present invention as compared to di(o-carboxynaphthol) phthaleins and unsubstituted phenanthrol/o-carboxynaphthol phthaleins absorb more strongly in the red and near infrared region of the visible spectrum and also show increased absorption in the blue and green region. The λmax and absorption measured at the λmax (Epsilon) was 673 nm (E = 17,700) for the compound of Example 1 as compared to 650 nm (E = 14,600) for Compound C and 662 nm (E = 17,000) for Compound C'. The optical transmission density for the compound of Example 2 was measured in the same way, and it was found that the spectral curve was similar to that of Example 1.

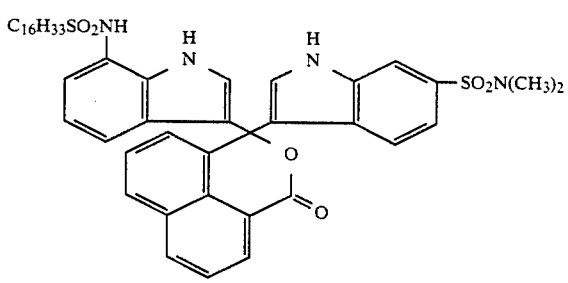

3-(7-n-hexadecylsulfonamidoindol-3-yl)-3-(6-dimethylsulfamoylindol-3-yl)naphthalide.

It will be apparent from a comparison of Curve 1 with Curve C in FIG. 3 that the processing composition containing the phthalein of the present invention affords more effective protection in the red and near infrared region of the visible spectrum as evidenced by the substantial increase in absorption above 650 nm, particularly in the 650 to 750 nm range.

In a further comparison, the absorptivity of aqueous alkaline processing compositions containing the compound of Example 1, the compound of Example 2 and Compound C, respectively, were measured before and after 6 days conditioning in an oven at 140° F. These three processing compositions were identical except for the phthalein optical filter agent and comprised a viscous aqueous alkaline solution of potassium hydroxide, titania pigment, N-butyl-α-picolinium bromide and 2% by weight of the respective phthalein optical filter agents. After removing the titania pigment by centrifugation, the visible spectra were measured spectrophotometrically and again after conditioning in the oven. The results for absorptivity per gram of composition at λmax(nm) are set out below:

| Compound  | Unconditioned | Conditioned  |
|-----------|---------------|--------------|
| Example 1 | 4.25 (λ672)   | 4.27 (λ672)  |
| Example 2 | 4.26 (λ672)   | 4.14 (λ672)  |
| Compound C| 2.74 (λ648)   | 2.34 (λ648)  |

In addition, the concentrations of the phthaleins, the quaternary compound and of the potassium hydroxide were measured for all of the samples after conditioning in the oven. These measurements indicated that the potassium hydroxide concentrations did not change but that the concentrations of the quaternary compound were lower in all of the aged samples by 10 to 15%. Though the concentrations of the phthaleins decreased by about 10% for the samples containing Examples 1 and 2, there was no evidence of the formation of addition products of the quaternary compound to the phenanthrol phthaleins and the absorption efficiency of the samples remained substantially the same as indicated above. In comparison, the concentration of Compound C decreased by about 15% and the attendant loss in absorptivity over the 6 day period indicated quaternary addition to this compound.

It will be understood that this invention is applicable to a wide variety of photographic processes employing any of various image-providing materials and that the transfer image may be in silver or in dye. Since such processes are now well known, it is not necessary to describe them in detail.

It will be understood that in any of these photographic systems, the transfer image may be positive or negative with respect to the photographic subject matter as a function of the particular image-forming system and that the silver halide emulsion may be negative-working or positive-working. Likewise, the image-receiving layer or other layers of the negative and positive components may vary as appropriate for a given process.

Since certain changes may be made in the above subject matter without departing from the scope of the invention herein involved, it is intended that all matter contained in the above description or shown in the accompanying drawings shall be interpreted as illustrative and not in a limiting sense.

I claim:

1. In a photographic film unit adapted for forming a transfer image viewable as a reflection print including a negative component comprising a photosensitive silver halide emulsion carried on a support; a positive component comprising an image-receiving layer carried on a transparent support; an acid-reacting layer disposed in at least one of said negative and positive components; and an aqueous alkaline processing composition comprising a light-reflecting pigment and at least one light-absorbing, pH sensitive optical filter agent releasably contained in a rupturable container positioned to release said composition for distribution between said negative and said positive components, the combination of said light-reflecting pigment and said optical filter agent being effective to prevent further exposure of said photosensitive emulsion during processing in the presence of radiation actinic to said emulsion and said light-reflecting pigment providing a layer after development which is effective to mask said photosensitive layer and provide a background for viewing the transfer image by reflected light;

the improvement which comprises employing as said processing composition, an aqueous alkaline solution comprising a light-reflecting pigment and as at least one said light-absorbing pH-sensitive optical filter agent, a pH-sensitive phthalein of the formula

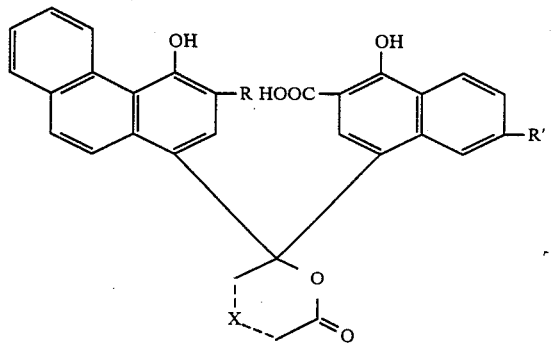

wherein R is alkyl having 1 to 6 carbon atoms, R' is alkoxy having at least 12 carbon atoms and X represents the carbon atoms necessary to complete phthalide or naphthalide.

2. A photographic film unit as defined in claim 1 wherein X completes naphthalide.

3. A photographic film unit as defined in claim 2 wherein said R is methyl.

4. A photographic film unit as defined in claim 3 wherein said R' contains 12 to 24 carbon atoms.

5. A photographic film unit as defined in claim 4 wherein said R' contains 22 carbon atoms.

6. A photographic film unit as defined in claim 1 wherein said processing composition additionally includes a viscosity imparting reagent.

7. A photographic film unit as defined in claim 1 wherein said light-reflecting pigment is titanium dioxide.

8. A photographic film unit as defined in claim 1 wherein said processing composition includes a light-absorbing, pH-sensitive indole phthalein optical filter agent.

9. In a photographic process for forming a diffusion transfer image viewable as a reflection print which includes the steps of applying a layer of aqueous alkaline processing composition comprising a light-reflecting pigment and at least one light-absorbing pH-sensitive optical filter agent between a negative component comprising an exposed silver halide emulsion carried on a support and a positive component comprising an image-receiving layer carried on a transparent support; said layer of processing composition being effective to develop said exposed silver halide emulsion and to form a visible image in said image-receiving layer and being effective to prevent transmission of light actinic to said silver halide emulsion during development thereof; and after a predetermined time, reducing the pH of said processing composition layer to a pH effective to decolorize said pH-sensitive optical filter agent; said pH reduction being effected by an acid-reacting layer disposed in at least one of said negative and positive components;

the improvement which comprises applying as said processing composition layer, an aqueous alkaline solution comprising a light-reflecting pigment and as at least one said light-absorbing pH-sensitive optical filter agent, a pH-sensitive phthalein of the formula

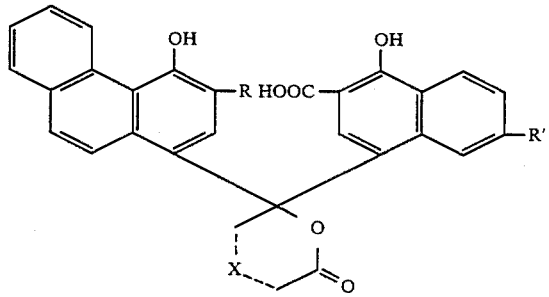

wherein R is alkyl having 1 to 6 carbon atoms, R' is alkoxy having at least 12 carbon atoms and X represents the carbon atoms necessary to complete phthalide or naphthalide.

10. A photographic process as defined in claim 9 wherein said X completes naphthalide.

11. A photographic process as defined in claim 10 wherein said R is methyl.

12. A photographic process as defined in claim 11, wherein said R' contains 12 to 24 carbon atoms.

13. A photographic process as defined in claim 12 wherein said R' contains 22 carbon atoms.

14. A photographic process as defined in claim 9 wherein said processing composition additionally includes a viscosity-imparting reagent.

15. A photographic process as defined in claim 9 wherein said light-reflecting pigment is titanium dioxide.

16. A photographic process as defined in claim 9 wherein said processing composition includes a light-absorbing, pH-sensitive indole phthalein optical filter agent.

17. A rupturable container for use in diffusion transfer film units adapted to provide transfer images viewable by reflected light, said rupturable container releasably holding an aqueous alkaline processing composition comprising an aqueous solution of alkali metal hydroxide, a light-reflecting pigment and at least one light-absorbing, pH-sensitive optical filter agent, at least one said optical filter agent being a pH-sensitive phthalein of the formula

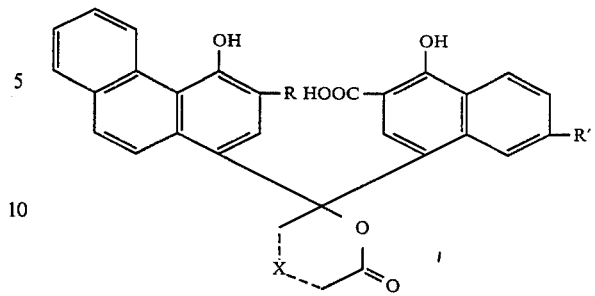

wherein R is alkyl having 1 to 6 carbon atoms, R' is alkoxy having at least 12 carbon atoms and X represents the carbon atoms necessary to complete phthalide or naphthalide.

18. A rupturable container releasably holding an aqueous alkaline processing composition as defined in claim 17 wherein said X completes naphthalide.

19. A rupturable container releasably holding an aqueous alkaline processing composition as defined in claim 17 wherein said R is methyl.

20. A rupturable container releasably holding an aqueous alkaline processing composition as defined in claim 19 wherein said R' contains 12 to 24 carbon atoms.

21. A rupturable container releasably holding an aqueous alkaline processing composition as defined in claim 20 wherein said R' contains 22 carbon atoms.

22. A rupturable container releasably holding an aqueous alkaline processing composition as defined in claim 17 wherein said processing composition additionally includes a viscosity-imparting reagent.

23. A rupturable container releasably holding an aqueous alkaline processing composition as defined in claim 17 wherein said light-reflecting pigment is titanium dioxide.

24. A rupturable container releasably holding an aqueous alkaline processing composition as defined in claim 17 wherein said processing composition includes a light-absorbing, pH-sensitive indole phthalein optical filter agent.

25. A compound having the formula

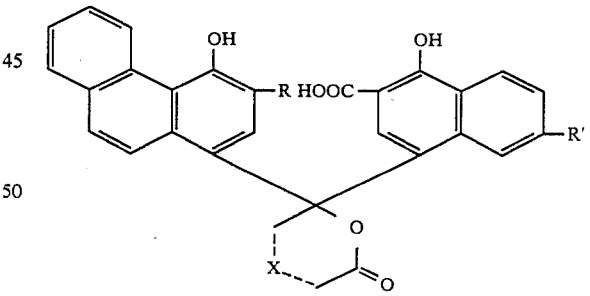

wherein R is alkyl having 1 to 6 carbon atoms, R' is alkoxy having at least 12 carbon atoms and X represents the carbon atoms necessary to complete phthalide or naphthalide.

26. A compound as defined in claim 25 wherein X completes naphthalide.

27. A compound as defined in claim 26 wherein said R is methyl.

28. A compound as defined in claim 27 wherein said R' contains 12 to 24 carbon atoms.

29. A compound as defined in claim 28 wherein said R' contains 22 carbon atoms.

30. A compound as defined in claim 28 wherein said R' contains 18 carbon atoms.

* * * * *